United States Patent [19]

Sanderson

[11] 4,105,407

[45] Aug. 8, 1978

[54] STERILIZING AND STORING MEDICAL ITEMS

[76] Inventor: Roger S. Sanderson, 24662 Santa Clara Ave., Dana Point, Calif. 92629

[21] Appl. No.: 710,522

[22] Filed: Aug. 2, 1976

Related U.S. Application Data

[63] Continuation of Ser. No. 571,263, Apr. 24, 1975, abandoned, which is a continuation-in-part of Ser. No. 501,183, Aug. 28, 1974, abandoned.

[51] Int. Cl.² ............................................. A61L 1/00
[52] U.S. Cl. .................................... 21/56; 21/94; 21/85; 220/257; 220/316; 49/165
[58] Field of Search .................. 21/2, 56, 44, 85–100, 21/103, 104, 82 R, 82 H, 83; 113/80 R, 800 A; 215/13; 220/201, 202, 209, 231, 257, 258, 278, 203, 316, 346; 236/47; 49/463, 465; 206/363, 438, 514, 515; 53/11, 12, 22 R, 167, 21 FC, 25, 111 R, 111 RC, 112 R; 141/8, 59, 61, 65

[56] References Cited

U.S. PATENT DOCUMENTS

| | | | |
|---|---|---|---|
| 812,968 | 2/1906 | Williams | 220/209 |
| 1,270,797 | 7/1918 | Dunkley | 53/112 R |
| 1,931,911 | 10/1933 | White | 53/12 |
| 1,946,872 | 2/1934 | Muhleisen | 220/231 X |
| 2,457,867 | 1/1949 | Chambers | 53/11 X |
| 2,715,251 | 8/1955 | Vischer | 21/98 |
| 2,997,397 | 8/1961 | Doulgheridis | 53/112 R X |
| 3,561,982 | 2/1971 | Oeth | 53/112 R X |

Primary Examiner—Norman Yudkoff
Attorney, Agent, or Firm—Knobbe, Martens, Olson, Hubbard & Bear

[57] ABSTRACT

A sterilizing container having a lid with an outer flange which cooperates with the upper edge of a base and a resilient member for sealing the container. The lid contains a mechanism for automatically moving the lid into sealing engagement with the base. Located on both the outer flange of the lid and the upper edge of the base are locking means which interact to place the lid in a sealing engagement with the base when the lid is moved by the moving mechanism on the lid. The container is designed to receive articles such as medical instruments which are sterilized when the container is placed in an autoclave, subjecting the instruments or articles to a sterilizing environment. The moving mechanism on the lid includes means responsive to the sterilizing environment to automatically bring the lid into sealing contact with the base prior to the return of the surrounding environment to ambient conditions, preserving the sterilized instruments until needed for use.

7 Claims, 10 Drawing Figures

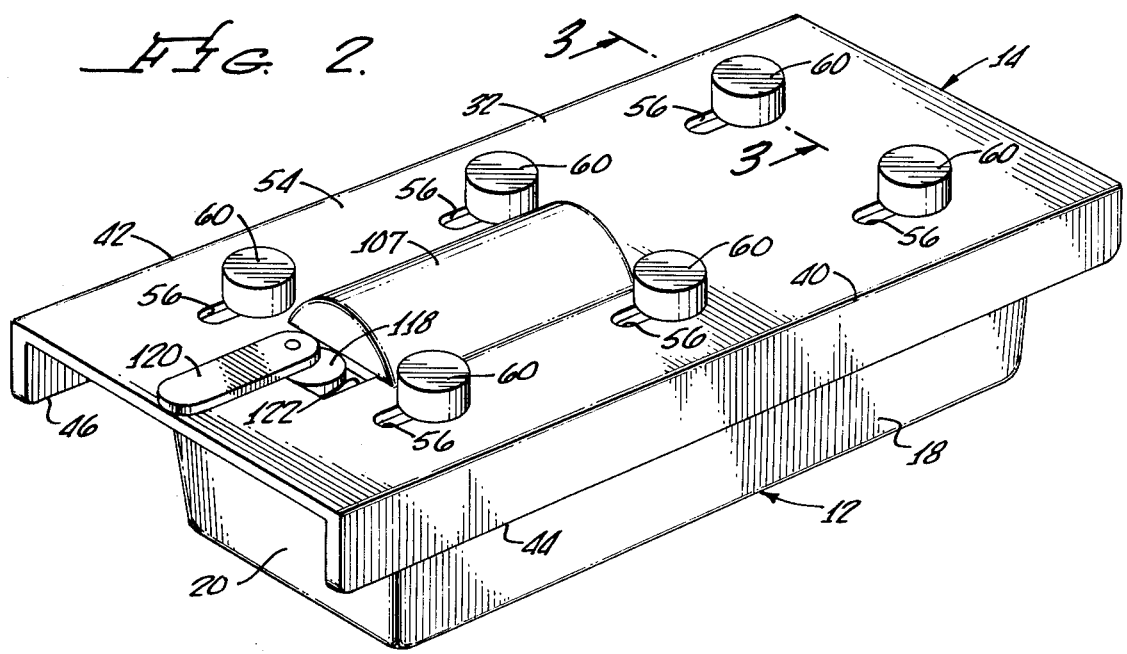
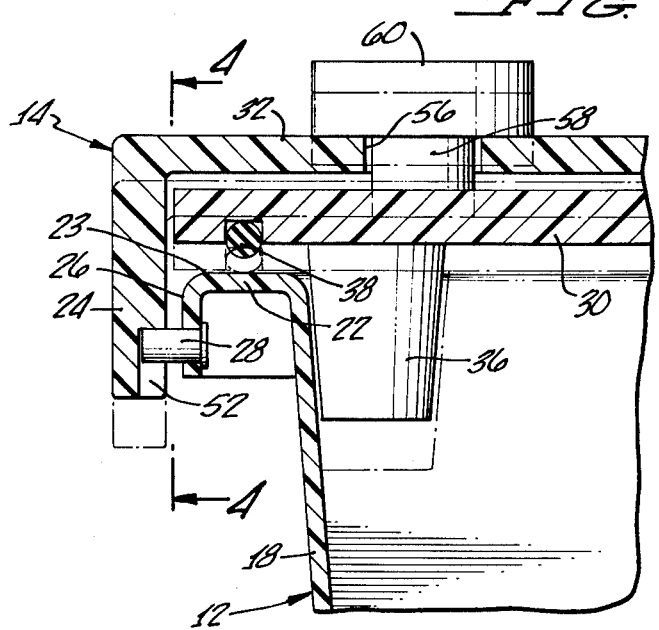

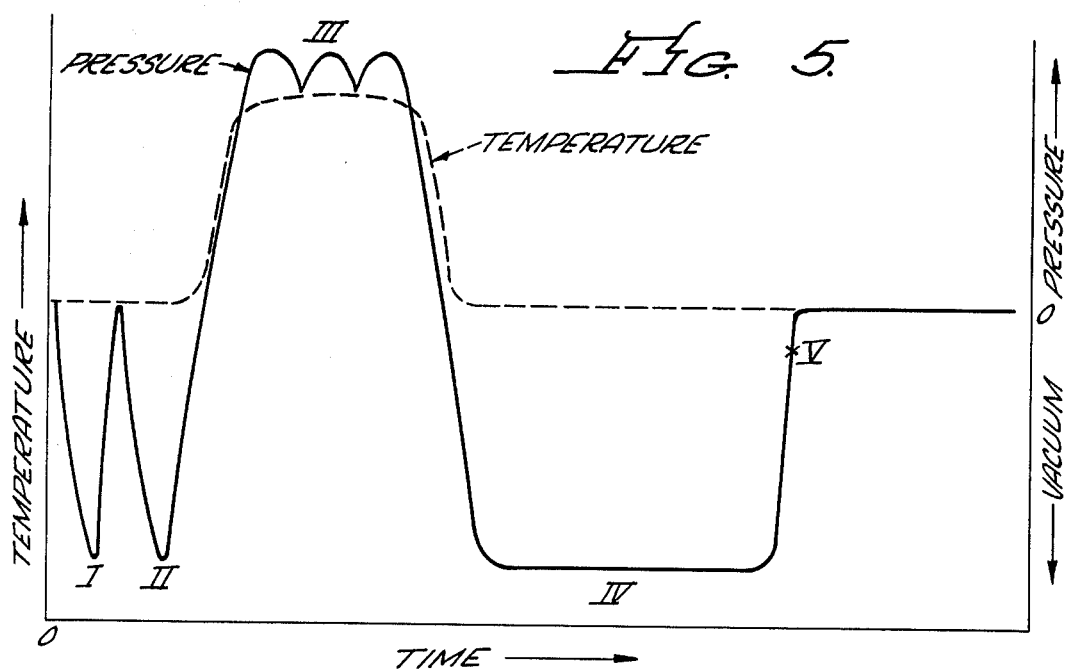
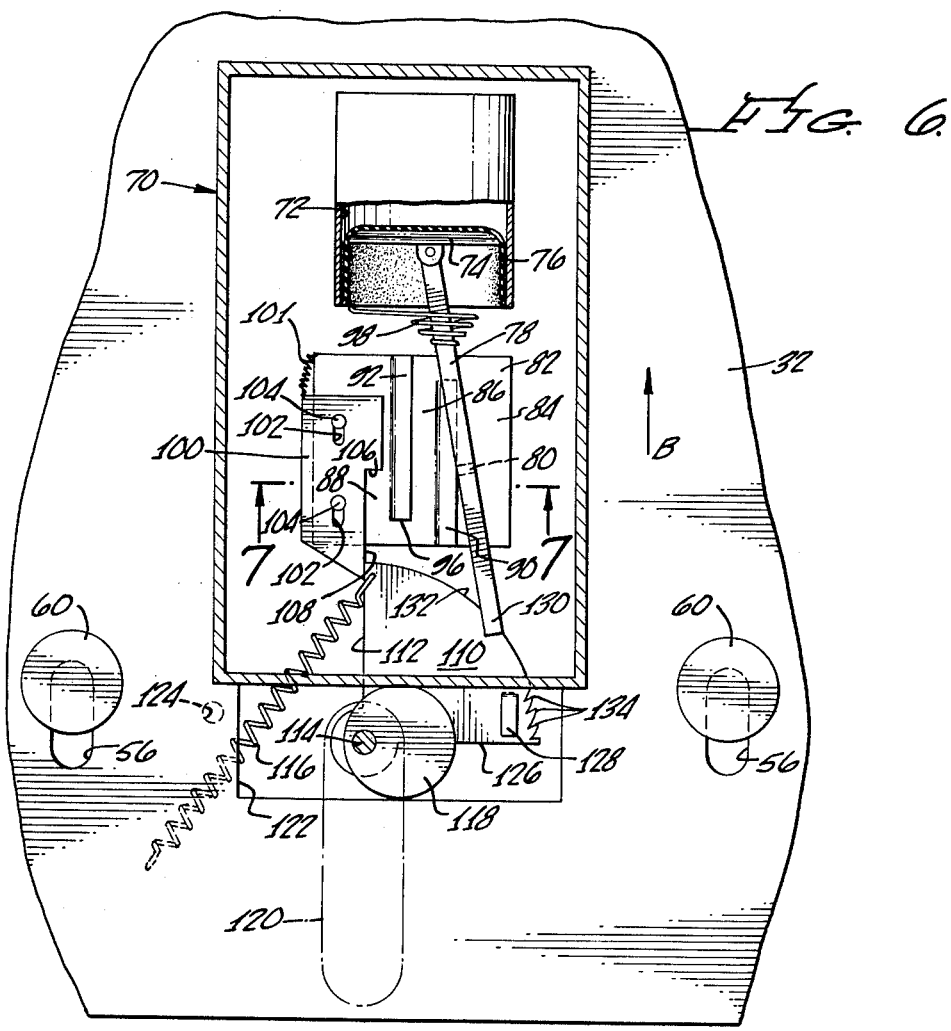

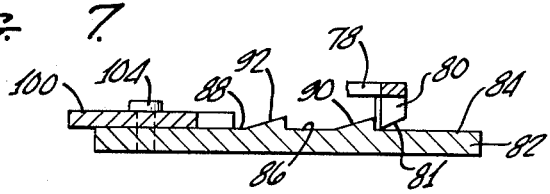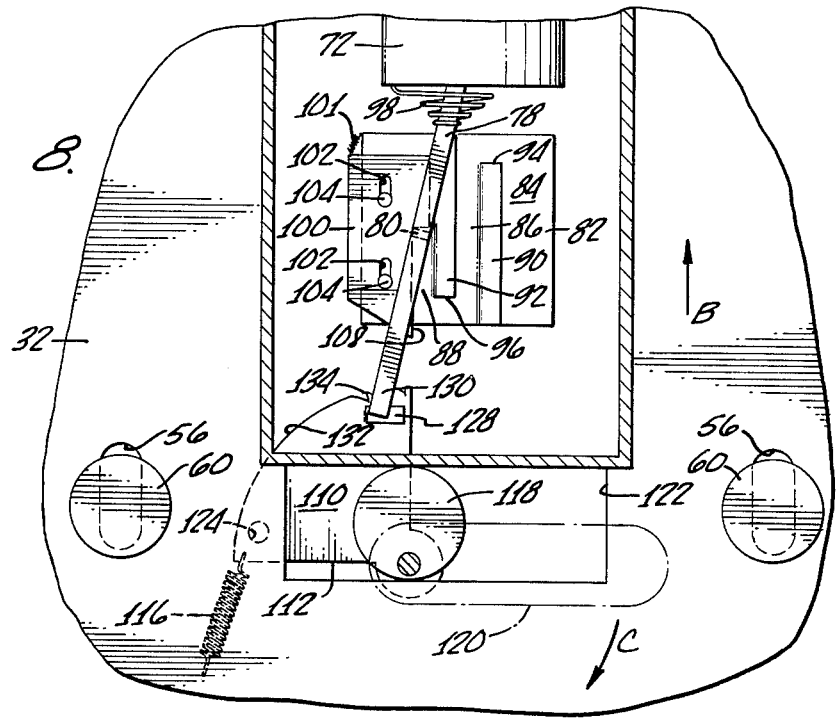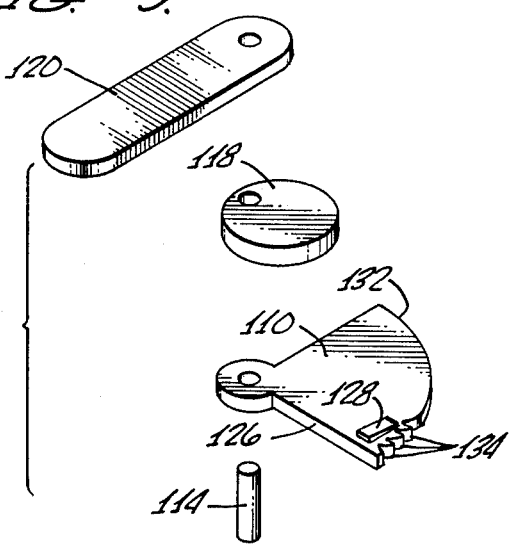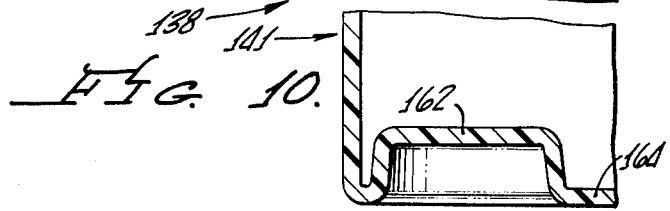

STERILIZING AND STORING MEDICAL ITEMS

RELATED APPLICATION

The present application is a continuation of patent application Ser. No. 571,263, filed Apr. 24, 1975, now abandoned, which is a continuation-in-part of a previous application entitled "Sterilizing and Storing Medical Items", Ser. No. 501,183, filed Aug. 28, 1974, now abandoned.

BACKGROUND OF THE INVENTION

The most commonly used method for sterilizing surgical instruments and other medical items is to place them in two towels which are enclosed in a sheet and taped shut for placement in a sterilizing autoclave. Steam within the autoclave easily penetrates the porous materials surrounding the instruments and sterilizes the instruments. The moisture is removed by a drying cycle in the autoclave. The sterile package of medical instruments is then loaded onto a plastic covered cart and transported through dirty hallways to less than sterile wards for use in hospital rooms or to be placed on a shelf for future use. If the pack has not been used in twenty days, it must be returned to the autoclave room for resterilization. Two-thirds of the sterilization workload in many hospitals is for items that were not used within the shelf life of the pack. The average cost expended in an autoclave load is fairly significant and presents a very inefficient process when considering the high percentage of nonuse, requiring expensive resterilization.

In addition to nonuse, another factor which reflects the shortcoming of the towel arrangement is that, unless the adequate labeling is used, the contents within the towel are unknown. Once the package is opened to check the contents, the sterilization is lost unless the contents are immediately used. Therefore, if the contents are not what the user desires, then the sterilization of that particular package must be repeated.

Some of the prior art have proposed the placing of the packs of instruments from the autoclave into plastic bags to keep contamination away and, hence, prolong the sterile shelf life of the package. These bags are vulnerable to puncture and contain contaminated room air when they receive the sterilized packages from the autoclave.

Although several attempts have been made to improve the system for containing sterilizing medical items, they have not proved to be satisfactory and the old approach of wrapping items in towels is believed to still be the method most widely used. U.S. Pat. No. 3,697,223-Kovalcik discloses a system which is a step in the right direction, but remains inadequate. That patent discloses a transparent plastic container, so that items are visible while within the container and the items can be sterilized if stored within the same container. However, a fundamental shortcoming of the arrangement disclosed in that patent is the inadequacy of maintaining sterilization. The lid is said to be tight fitting, but it does not actually provide a seal between the lid and cover. It is suggested that autoclaving tape is utilized to seal the lid to the container; however, such tape does not provide a permanent seal. More significantly, that patent shows holes in the lid for circulation during sterilization and no provision is made for closing the holes. Thus a tight fit between the lid and the container or the use of tape would seem to be of no avail.

SUMMARY OF THE INVENTION

The present invention comprises a reusable container which will automatically seal itself in response to certain specified environmental conditions in which it is subjected. The container has means for providing access to its interior for the insertion or removal of various objects.

The preferable embodiment of this invention has a base and a lid which are automatically moved into sealing engagement after being subjected to a sterilizing environment. Included within the flange of the lid and the upper edge of the base portion are locking means which cooperate to bring the lid into sealing engagement. The lid is comprised of two portions which are movable relative to each other in response to a moving means situated on the lid. One portion of the lid remains stationary when positioned within the base portion of the container while the other portion moves relative to the container to bring the lid into sealing engagement with the base portion of the container.

The moving means located in the lid comprises a programmer and a triggering mechanism to quickly and forcefully move the lid into the sealing engagement with the base portion of the container. The programmer is designed to trigger the movement of the lid at a specific time within the cycle of sterilization within an autoclave. A large gasket surrounding the perimeter of the base portion of the container provides the sealing means between the lid and the base portion. The moving means on the lid is driven by a spring biased driving mechanism which is released by the trigger mechanism to force the lid in its locking direction.

The use of a clear sturdy reusable container that can withstand the temperatures of pressures within the sterilizing environment of the autoclave provides an ideal method of maximum efficiency and minimum cost of sterilizing and storing supplies. The container and lid arrangement is designed to allow the sterilizing steam to penetrate or permeate the entire box and also allow full drying cycle of the contents within the box. However, the moving means automatically activates to seal the lid on the base portion of the container prior to the opening of the autoclave door and the return to ambient temperature conditions. This seal provides a slight vacuum in the box until it is manually open for use of the contents of instruments therein. The shelf life of such a box is as long as the vacuum is maintained. The box eliminates the need for resterilization of unused items every twenty days. It also allows the user of the contents to see what is within the box, eliminating many misopened parcels that now find their way back to the use of the autoclave room unnecessarily. The box also provides a desirable sterile environment for shipment of articles such as heart valves and other metal prostheses.

BRIEF DESCRIPTION OF THE DRAWINGS

FIG. 2 is a perspective view of the container with the lid placed on the base;

FIG. 3 is a partial sectional view taken along the lines 3—3 in FIG. 2;

FIG. 5 is a schematic graphical rendition of the general environmental stages within the autoclave;

FIG. 6 is a plan view of the moving means on the lid in the cocked position;

FIG. 7 is a sectional view taken along the lines 7—7 in FIG. 6;

FIG. 8 is a plan view of the moving means located on the lid with the lid in its sealed engagement;

FIG. 9 is an exploded view of the driving mechanism for the lid; and

FIG. 10 is a sectional view of an alternate embodiment of a sealing arrangement.

DETAILED DESCRIPTION OF THE INVENTION

Figure 1:
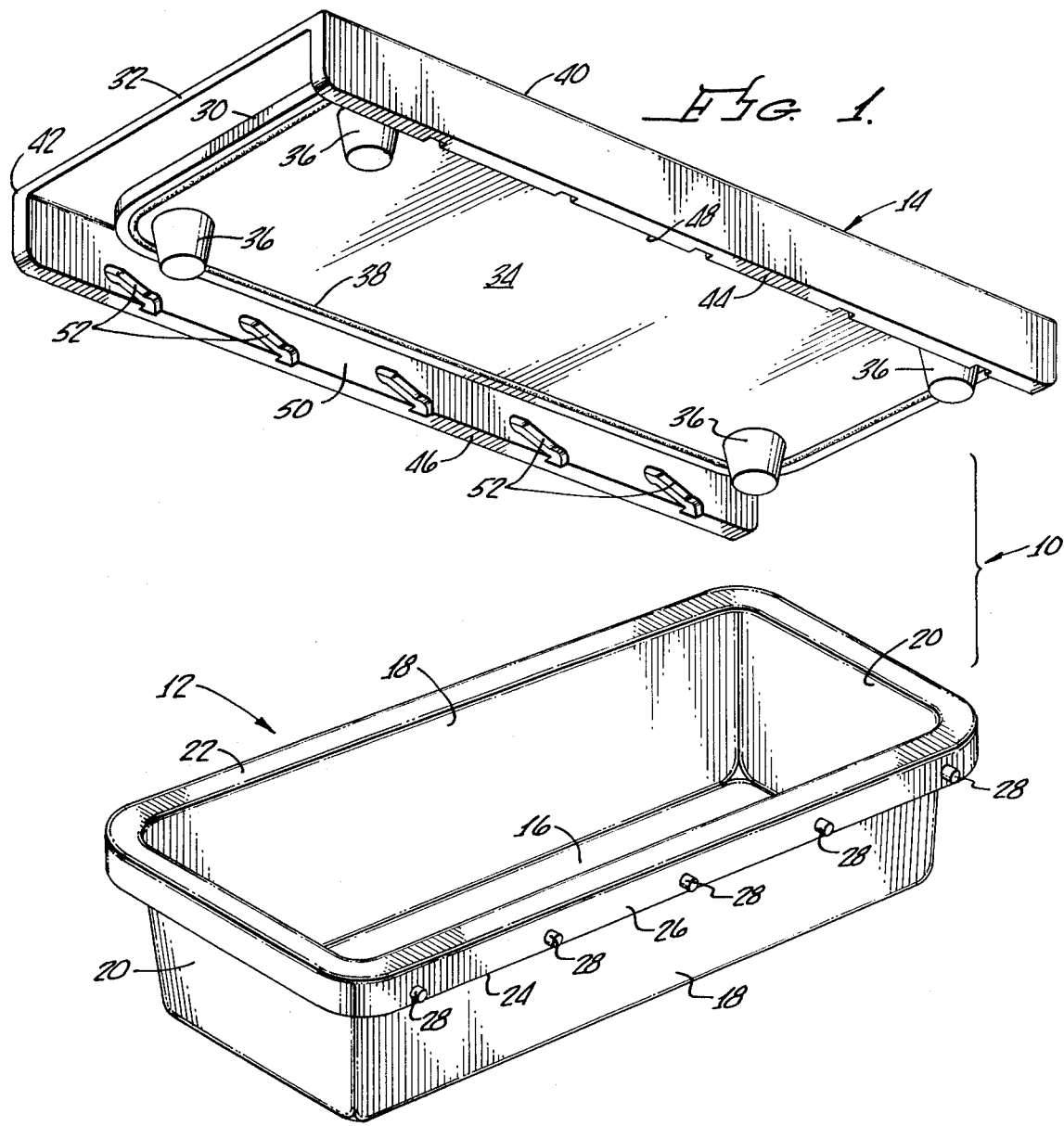
FIG. 1 is a perspective view of the container showing the base and lid.

With reference to FIG. 1, the applicant's container invention 10 is shown having a base 12 and a lid 14. The base 12 has a general rectangular box configuration with a bottom support surface 16 with upwardly extending side walls 18 and end walls 20. The top perimeter or flange 22 of the base 12 extends horizontally outward from each of the walls 18 and 20 and supports a downward extending flange 24 around the entire perimeter of the base portion 12. The vertical outside surface 26 of the downward extending flange 24 has a series of outwardly extending horizontal pins 28 along the perimeter of the base adjacent each of the side walls 18.

The lid 14 is comprised of two sections, an anchoring section 30 and a sliding section 32, which are movable with respect to each other. Mounted on the bottom surface 34 of the anchoring section 30 are a series of anchoring feet 36 positioned at each corner of the rectangular shaped anchoring section 30. These anchoring feet are designed to fit closely adjacent the corners in the base 12 where the side walls 18 and end walls 20 intersect to prevent any relative movement between the anchoring section 30 and the base 12. Also mounted on the bottom surface 34 of the anchoring section 30 is a sealing gasket 38 which extends around the entire perimeter of the anchoring section 30 to provide sealing engagement with the flange 22 of the base 12.

Being larger, the sliding section 32 of the lid 14 is slidably mounted over the anchoring section or portion 30. The longitudinal edges 40 and 42 of the generally rectangular shaped sliding section 32 have downwardly extending outside flanges 44 and 46 respectively. Recessed within the respective inside surfaces 48 and 50 of the outside flanges 44 and 46 are a series of locking grooves 52 which are designed to receive the pins 28 when the lid 14 is placed over the base 12.

The top surface 54 of the sliding section 32 is shown more clearly in FIG. 2. Placed within the sliding section 32 are a series of slots 56 which allow the sliding section 32 to move relative to the anchoring section 32. A series of guide posts 58 as shown in FIG. 3 are fixed to the anchoring section 30 of the lid and extend up through each of the slots 56 in the sliding section 32. An enlarged head 60 is mounted on each of the guide posts 56 in order to maintain the connection between the anchoring section 30 and the sliding section 32. Consequently, it can be seen that, although the sliding section 32 is connected to the anchoring section 30 of the lid 14, the slots 56 allow for the relative movement between the respective sliding and anchoring sections.

Figure 4:
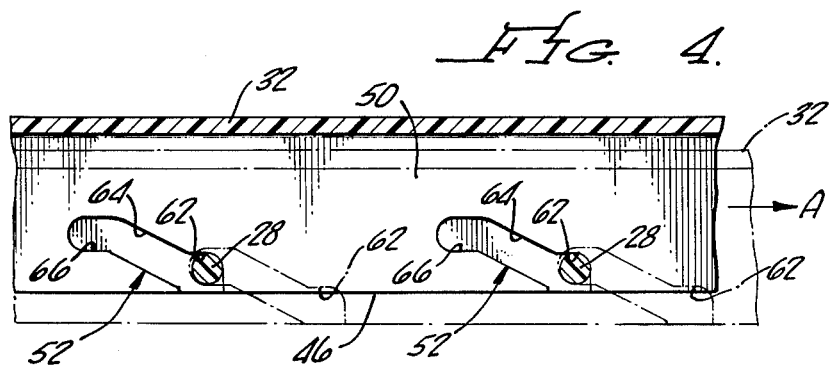
FIG. 4 is a partial sectional view taken along the lines 4—4 in FIG. 3.

The cooperative relation between the pins 28 on the base 12 and the locking slots or grooves 52 in the lid 14 is shown more clearly in FIG. 4. When the lid is initially placed on the base 12, the pins 28 will hold the lid 14 in a generally open position, allowing a space between the anchoring section 30 with its seal 38 and the flange 22 on the base as shown in solid lines in FIG. 3. This is accomplished with respect to FIG. 4 by the resting of the first horizontal surface 62 of the locking groove 52 on the pin 28. When the sliding section 32 of the lid 14 is forced to move in the direction of the arrow A, the pins 28 will ride up through the cam passage 64 of the groove 52 and onto a second horizontal surface 66. In this position, the overall lid including both the sliding section 32 and the anchoring section 30 have been forced downward into closer engagement with the base 12. This results in the gasket 38 as shown in FIG. 3 providing a sealing engagement with the flange 22 of the base 12. The resultant placement of the lid is shown in phantom in both FIGS. 3 and 4. It should be noted that, while the sliding section 32 of the lid moves both in a horizontal and downward direction, the anchoring section 30 of the lid moves downward to cause the gasket 38 to tightly seal against the surface of the flange 22 of the perimeter of the base 12. The pins 28 will be tightly bearing against the second horizontal surface to maintain the sealing engagement of the gasket 38 on the flange 22.

With respect to FIG. 6, the lid 14 contains an opening mechanism 70, which operates in response to the surrounding environment of the container 10. The opening mechanism 70 utilizes a sealed chamber 72 mounted on the sliding section 32 of the lid 14 and having as one of its walls a flexibly connected piston head 74. The bellows 76 provides the desired flexibility. The piston head 74 is connected to a piston rod 78 on which is mounted a pawl 80 as shown more clearly in FIG. 7. The pawl 80 rests on a program block 82 mounted on the sliding section 32 of the lid 14. The program block 82 contains a series of program paths 84, 86 and 88 as shown in both FIGS. 6 and 7. These program paths are divided by the ridges 90 and 92. Access between the respective program paths 84 and 86 in the same plane is provided by a pathway adjacent the end 94 of the ridge 90 closest the sealed chamber 72. Similarly, access between the respective program paths 86 and 88 is provided by a path adjacent the end 96 of the ridge 92 furthest from the sealed chamber 72. The piston rod 78 is spring biased in both a downward direction toward the program block 82 and a direction toward the program path 88 by a spiral spring 98 which is mounted around the piston rod 78 adjacent the piston head 74 and having its inner end connected to the piston rod 78 and its outer end connected to the sealed chamber 72.

Slidably mounted on the program block 82 adjacent the program path 88 is a trigger member 100 having slots 102 which receive the anchoring pins 104 mounted in the program block 82. The trigger 100 is biased in a direction away from the sealed chamber 72 by a spring 101. Trigger member 100 has an activating edge 106 and a retaining edge 108. The functions of these edges will be explained in more detail below.

As shown in FIG. 2 a half cylindrical cover 107 covers the sealed chamber 72, the program block 82, and trigger member 100.

Pivotally mounted adjacent the trigger member 100 is a detent sector 110, having a lead edge 112 which contacts the retaining edge 108 of the trigger member 100. The detent sector is mounted on a pivot pin or shaft 114 fixed to the anchoring section 30 of the lid 14 and is biased by the coil spring 116 to move in a counterclockwise direction as viewed in FIG. 6 about the pivot pin 114. The detent sector 110 moves within a recessed area (not shown) in the anchoring section 30 of the lid, because the detent sector rotates in a plane below the sliding section 32 of the lid. Similarly mounted on the pivot pin 114 is an eccentric drive member 118 and a cocking handle 120 shown in more detail in FIG. 9. Although shown in a separated orientation in FIG. 9, the cocking handle 120, the eccentric drive 118, and the detent sector 110 are attached in a fixed relation with respect to each other pivot as a unit about the pivot pin 114. It should be noted with respect to FIG. 6 that the eccentric drive 118 is mounted on the pin 114 at a point located approximately half the distance between the center and the circumference of the circular eccentric drive member 118, so that the drive 118 will pivot off center. The eccentric drive member 118 is situated within a drive cavity or slot 122 located in the sliding section 32 of the lid 14. Consequently, any rotation by the eccentric drive 118 around the pivot pin 114 is retained by the boundaries of the drive slot 122. It should be noted that the pivot pin 114 is fixed to the stationary section 30 of the lid 14. Therefore, the only situation in which the eccentric drive is allowed to pivot around the pin 114 is if the moving section 32 of the lid slides longitudinally over the base 12 to allow the eccentric drive 118 to rotate in a general counterclockwise direction with respect to FIG. 6. Since the detent sector 110 and the cocking handle 120 are fixed to the eccentric drive 118, movement by either the detent sector 110 or the cocking handle 120 will result in a responsive similar angular movement by the eccentric drive member 118.

Situated on the lid 14 is a relief valve 124 which is designed to relieve the internal vacuum within the sterilizing box when it is desired to remove the lid and gain access to the sterilized instruments therein. Otherwise, great difficulty may be encountered in trying to remove the lid subjected to a vacuum.

Turning to the operation of the present invention, reference is made to FIGS. 1 and 4 wherein the instruments to be sterilized are placed on the bottom support surface 16 of the base and the lid 14 is positioned on the flange surface 22 in such a manner that the anchoring feet 36 are located adjacent each corner of the base of the box where the longitudinal surfaces 18 intersect the end surfaces 20. Consequently, the anchoring section 30 of the lid 14 will not move in a longitudinal direction with respect to the base portion 12 of the box 10. In this particular orientation, the first horizontal surface 62 of each of the locking slots 52 rests on each of the respective pins 28, so that the lid is spaced from the upper flange 22 on the base portion 12. Consequently, the interior area of the box bounded by the bottom 16, the sides 18 and 20, and the bottom surface 34 of the anchoring section 30 of the lid 14 is in fluid communication with the outside environment surrounding the outside of the box 10. The box with the lid positioned in this first or elevated position on the base 12 is placed in an autoclave for exposing the instruments located in the base portion 12 to a sterilizing environment.

To more clearly understand the environment for sterilizing instruments in a pressurized autoclave, reference is made to FIG. 5 generally showing the environmental changes occurring during the various stages in the autoclave sterilization process. Although the increased temperature experienced within the autoclave actually provides the sterilizing environment, particular attention is directed to the pressure variations which are important with respect to the operation of the closing device 70 in FIG. 6. It must be remembered that the sealed chamber 72 is sealed from the environment surrounding it and, therefore, the movable piston head 74, which is connected by the bellows 76 to the sealed chamber, will move depending upon the relative differences between the outside surrounding pressure environment and the pressure within the sealed chamber 72.

The first stage in the autoclave process shown in FIG. 5 at I is a first prevacuum condition in order to evacuate contaminated air from within the box and the autoclave itself. The environment again returns to ambient conditions after the prevacuum stage I by the introduction of clear filtered air. The second stage II of prevacuum environment is established where the air within the autoclave and the box is evacuated in order to be assured that no contaminated air remains within the environment inside the autoclave. During both of these prevacuum stages I and II, the pressure within the sealed chamber 72 will be greater than the outside environment which, therefore, will cause the piston head 74 to move toward the program block 82 in FIG. 6, resulting in the piston rod 78 and the pawl 80 moving further away from the sealed chamber 72. The position of the pawl 80 in FIG. 6 is basically at ambient conditions, so that, when subjected to the first prevacuum environment I as shown in FIG. 5 the piston head 74 will move the pawl along the program path 84 further away from the sealed chamber 72. When the environment returns back to ambient condition as shown on FIG. 5 between the two prevacuum environments I and II, the pawl 80 will again return to its position as shown in FIG. 6. In the second prevacuum condition II, the pawl will again move further away from the sealed chamber 72 along the program path 84.

The next stage in the autoclave process is the high temperature/pressure environment III where both the pressure and the temperature build to higher levels than ambient conditions in order to provide the sterilizing atmosphere. It is during environment III that the sterilizing steam enters the interior of the box 10 through the space between the lid 14 and the base 12 to contact and sterilize the articles therein. When the pressure reaches the levels or amounts shown with respect to environment III in FIG. 5, the pressure of the surrounding environment will be greater than the pressure within the sealed chamber 72 of FIG. 6, so that the piston head 74 will move further into a recessed position within the sealed chamber 72, causing the pawl 80 to move closer to the sealed chamber 72 adjacent the edge 94 of the ridge 90 in the program block 80. Because the piston rod 78 is biased in a direction toward the trigger member 100, the pawl will move over to program path 86 adjacent the ridge 92.

As the pressure decreases and enters a vacuum drying stage IV shown in FIG. 5, the pawl 80 in FIG. 6 will move downward along program path 86 to a position adjacent the end 96 of the ridge 92. This movement of the pawl is caused by the fact that the surrounding environment again will be of a lesser pressure than within the sealed chamber 72, so that the movable piston head 74 will move in a direction toward the program block 82, causing the pawl to move a similar distance. Because the pawl is spring biased by the spring 98 in a direction toward the trigger member 100, the pawl and piston rod 78 will move into program path 88 adjacent the trigger member 100. As the vacuum drying stage IV is completed and the surrounding vacuum environment again begins to return to ambient pressure, the piston head 74 in FIG. 6 will move away from the program block 82 causing the pawl 80 and piston rod 78 to move toward the sealed chamber 72.

The pawl 80 will ride along the restraining edge 108 of the trigger member 100 as it proceeds toward the sealing chamber 72. Just before the surrounding environment reaches ambient condition, the pawl 80 will contact the trigger surface 106 of trigger member 100 at point V in FIG. 5 just below ambient pressure. The continued movement of the pawl toward the sealed chamber 72 will cause the trigger member 100 to slide against spring 101 in slots 102 on the retaining pins 104 in a direction toward the sealed chamber 72. This will cause the restraining surface 108 of the trigger member 100 to release the detent sector 110 and allow the spring 116 to forcefully rotate the detent 110 in a counter-clockwise direction in FIG. 6 approximately 90°.

Because the eccentric drive 118 is fixed to the detent sector 110, the movement of the detent sector will cause a corresponding movement of the eccentric drive. The movement of the eccentric drive 118 is possible because the drive cavity 122 is located in the movable section 32 of the lid 14 which slides in the direction of the arrow B shown in FIG. 6 and 8. This is possible, since the slots 56, which are in the movable sector 32, are of sufficient length to allow the eccentric drive to rotate the approximately 90° along with the detent sector 110. The movement of the movable section 32 of the lid in the direction of the arrow B in FIGS. 6 and 8 causes the pins 28 in FIGS. 1 and 4 to ride into the locking slots 52 along the surface 64 and onto the second horizontal surface 66, locking the lid 14 in a sealed engagement with the base 12 of the box 10. The sealed position of the lid 14 with the gasket 38 against the flange 22 is shown more clearly in phantom in FIG. 3. The closing of the lid 14 to be sealed engagement with the base 12 just prior to the return of ambient conditions will place the interior of the box 10 under a slight vacuum.

The resultant position of the movable portion of the lid 32, the detent sector 110, the eccentric drive 118 and the cocking handle 120 is shown in FIG. 8. With respect to FIG. 9, located adjacent the trailing edge 126 of the detent sector 110 is a ramp 128 which extends up above the general horizontal plane of the detent sector 110. This ramp 128 is designed to receive the free end 130 of the piston 78 as shown in FIG. 8. Located on the outer perimeter 132 of the detent sector 110 adjacent its trailing edge 126 are a series of safety catches 134 which are designed to contact the restraining edge of the trigger member 100 to prevent the detent sector 110 from returning to its sealed position if someone should inadvertently move the cocking handle 120 in a clockwise direction a few degrees, exposing the interior of the box to contaminated air through the relief valve 124 which is sealed by the detent sector 110. Consequently, if someone should inadvertently move the cocking handle, one of the safety catches 134 would contact the trigger member 100, preventing the detent sector 110 from returning to its apparent sealed position, notifying a possible user that the instruments are no longer sterile. The spring biased trigger 100 would return to its biased position toward the detent sector 110, because any clockwise movement of the detent sector 110 in FIG. 8 would cause the ramp 128 to contact the free end 130 of the piston rod 78 and move the pawl away from the trigger member 100 as the detent sector is rotated clockwise.

Once the instruments within the box have been subjected to a sterilizing environment and the lid has been automatically sealed onto the base of the box 10, the box is removed from the autoclave and put in a storage area until the sterilized instruments contained therein are needed for use. Anyone desiring to use the instruments simply moves the cocking handle 120 as shown in FIG. 8 in the direction of the arrow C clockwise which causes both the eccentric drive 118 and the detent sector 110 to also rotate in a clockwise direction. Once the detent sector 110 is moved from above the relief valve 124 in the anchoring section 30 of the lid 14, the slight vacuum which is inside the container is relieved to thereby allow easier continued rotation of the eccentric drive 118 in its clockwise direction to move the lid in a direction opposite the arrow B. The pins 28 in FIGS. 1 and 4 ride down the slope 64 to their position adjacent the first horizontal surface 62 in the locking guides 52. The cocking handle 120 is moved to its position shown in FIG. 6 so that the detent sector is again restrained against the bias of the spring 116 by the restraining edge 108 of the trigger member 100. Furthermore, the ramp 128 on the detent sector 110 moves the pawl 80 along with the piston rod 78 against the bias of the spring 98 to its original position in the program path 84 of the program block 82. With respect to FIG. 7, the upward sloped surfaces of the ridges 90 and 92 in conjunction with the similarly sloped bottom surface 81 of the pawl allow for the easy movement of the pawl 80 to the passage 84.

When the cocking handle is positioned as shown in FIG. 6, the user can remove the lid 14 and retrieve the sterilized instruments from therein. The box 10 is then ready for re-use in holding instruments to be sterilized in an autoclave in storage thereafter. The sequence of operation as discussed above is then repeated.

One area of concern when taking the sterilized instruments from the box 10 relates to the user brushing against a part 23 of the surface of flange 22 in FIG. 3 which is outside the gasket 38 and, therefore, is not sterilized. This could cause the user to inadvertently contaminate the instruments. Consequently, an alternate embodiment for the sealing arrangement is shown in FIG. 10 on box 138 which is designed to eliminate this possibility of contamination.

The upper perimeter 140 of the base 141 on box 138 is narrower than the perimeter 22 of the embodiment 10 shown in FIG. 1. Extending down from the perimeter 140 in FIG. 10 is a vertical flange 142 which supports a lower horizontal sealing support flange 144. Located on the support flange 144 is a sealing gasket 146. Extending up from the support flange 144 outside the gasket 146 is a mounting flange 148 on which are attached pins 150 which operate in conjunction with the locking guides (not shown) in the sliding section 154 of the lid 156 and the same manner as described with respect to FIGS. 1 and 4.

The sliding section 154 of the lid 156 in FIG. 10 is similar to sliding section 32 of lid 14 in FIG. 1; however, the anchoring section 158 in FIG. 10 has a modified configuration. Along the outer perimeter of the anchoring section 158 is a downward extending engaging member 160 which is designed to seal against the gasket 146 when the locking guides move relative the pins 150 to pull the lid 156 down onto the base 141. The lid 156 supports the same moving means 70 shown in FIGS. 6 through 9 which activates lid 156 in the same manner as lid 14. The overall configuration and operation of the alternate box 138 is the same as box 10 except for the above described sealing arrangement.

Because of this sealing arrangement, a user of the sterilized instruments will not inadvertently contaminate the instruments since the perimeter 140 which he may brush against has also maintained its sterilization, since it is inside the gasket 146.

Another feature of box 138 is the placement of a series of recessed dimples 162 in the bottom 164 of the box. These dimples are designed to receive a similar number of guide post heads 166 on each of the guide posts 168, connecting the anchoring section 158 and sliding section 154 of the lid 156. This provides a convenient stacking ability between respective boxes 138 where stacked on each other. Similar dimples (not shown) are located in bottom 16 of the box 10 in FIG. 1 to receive the guide post heads 60 of the guide posts 58 in FIG. 3 to allow convenient stacking of boxes 10.

It should be noted that other embodiments of sterilizing boxes are possible utilizing the principles disclosed in the present invention. An alternate sterilizing box can be constructed using a manual latch holding mechanism on the lid in conjunction with a valve system in the box to seal at the correct stage in the autoclave process to maintain the sterilized environment for medical instruments in the box for as long as desired. The mechanism 70 could of course be used to operate a valve in the box rather than move a lid.

What is claimed is:

1. A method of sterilizing items comprising the steps of:
   placing said items in a rigid reusable container which can be repeatedly subjected to steam;
   placing the container in an autoclave with the container sufficiently open so that the exterior of the container is in fluid communication with the interior;
   operating the autoclave to provide a sterilizing cycle including a vacuum environment to withdraw the air from the container followed by a pressure steam environment to sterilize the items, and a final vacuum environment to withdraw the steam from the container and dry the articles in the container; and
   automatically sealing said container by means responsive to the environment in the autoclave after the articles have been sterilized but before the final vacuum environment is complete.

2. A method of sterilizing articles comprising the steps of:
   placing said articles in an open ended container;
   positioning a lid loosely on said container so that said articles are exposed to an environment surrounding said container;
   placing said container in a sterilizer;
   introducing a sterilizing environment into said sterilizer;
   after introducing said sterilizing environment, applying a vacuum to the sterilizer exterior to withdraw the environment from said container; and
   automatically moving said lid to a sealed position on said container after said articles are sterilized by said sterilizing environment prior to the return of ambient conditions within said sterilizer.

3. A method of sterilizing articles as defined in claim 2 wherein the step of automatically moving said lid to a sealed position is reponsive to gaseous pressure changes within said sterilizer.

4. A method of sterilizing articles as defined in claim 2 wherein the step of automatically moving said lid to a sealed position is responsive to temperature changes within said sterilizer.

5. A container for for sterilizing articles in an enclosed sterilizing said container comprising:
   a container base having an open side for receipt of said articles;
   a lid for engagement with said open side of said base for sealing said container after exposure to said sterilizing environment;
   means forming a part of said lid and said base for retaining said lid on said base in an open position, wherein said articles within said container are exposed to said sterilizing environment when such an environment is applied to the exterior of the container;
   means on said container for moving said lid to a closed position sealing said articles within said container; and
   pressure responsive means for sensing the application of a vacuum to the exterior of the container which withdraws said sterilizing environment and means for automatically actuating said moving means to close said container in response to said sensing means after said articles in said container have been sterilized.

6. Apparatus for containing articles while they are being sterilized and stored comprising:
   first and second container portions defining a container for receiving said articles;
   means for retaining said second portion in open position with respect to said first portion so that the interior and exterior of the container are in communication; and
   pressure sensing means mounted on said container responsive to the application of a pressurized sterilizing environment to said container and the withdrawal of said environment from the container, said sensing means including means cooperating with said retainer means to automatically seal said second container portion on said first portion after said sterilizing environment has been withdrawn from the container but before the pressure on the exterior of the container is returned to ambient pressure.

7. The apparatus of claim 6, wherein said container is made of a transparent plastic material which can stand the pressure and temperature of a sterilizing cycle in an autoclave, and said container is sized to be conveniently positioned within existing autoclaves with one or more similar containers.

* * * * *